United States Patent
Vysokov et al.

(10) Patent No.: US 12,274,560 B2
(45) Date of Patent: Apr. 15, 2025

(54) SYSTEM AND METHOD FOR IMPLEMENTING A STIMULATION PROTOCOL

(71) Applicant: Brainpatch Limited, London (GB)

(72) Inventors: Nickolai Vysokov, London (GB); Illya Tarasenko, London (GB); Dauren Toleukhanov, London (GB)

(*) Notice: Subject to any disclaimer, the term of this patent is extended or adjusted under 35 U.S.C. 154(b) by 481 days.

(21) Appl. No.: 17/350,447

(22) Filed: Jun. 17, 2021

(65) Prior Publication Data
US 2021/0307684 A1 Oct. 7, 2021

Related U.S. Application Data

(63) Continuation-in-part of application No. 17/413,310, filed as application No. PCT/IB2019/060767 on Dec. 13, 2019.

(30) Foreign Application Priority Data

Dec. 14, 2018 (GB) .................................... 1820468
Jun. 17, 2020 (GB) .................................... 2009267

(51) Int. Cl.
*A61B 5/00* (2006.01)
*A61B 5/256* (2021.01)
(Continued)

(52) U.S. Cl.
CPC ............ *A61B 5/4848* (2013.01); *A61B 5/256* (2021.01); *A61B 5/291* (2021.01); *A61B 5/372* (2021.01);
(Continued)

(58) Field of Classification Search
CPC ....... A61B 5/4848; A61B 5/372; A61B 5/256; A61B 5/291; G16H 10/60
See application file for complete search history.

(56) References Cited

U.S. PATENT DOCUMENTS 6,463,328 B1  10/2002  John
8,958,882 B1  2/2015  Hagedorn
(Continued)

FOREIGN PATENT DOCUMENTS

CN  106310517 A  1/2017
CN  110368577 A  * 10/2019
(Continued)

OTHER PUBLICATIONS

Search Report under Section 17(5) issued in GB Application GB1820468.5 on Jun. 17, 2019, 4 pages.
(Continued)

*Primary Examiner* — Tammie K Marlen
*Assistant Examiner* — Maria Catherine Anthony
(74) *Attorney, Agent, or Firm* — RC Trademark Company

(57) ABSTRACT

There is disclosed a system for implementing a stimulation protocol that, when in operation, mimics an effect of at least one drug on the brain of a user under treatment for a disease, or for mental well-being applications, wherein the system comprises:
(i) a brain interfacing apparatus that
records electroencephalogram (EEG) of the user before and after taking the drug; and
provides at least one stimulation to the brain of the user, wherein the at least one stimulation is provided to achieve the effect similar to the at least one drug; and
(ii) a monitoring device that enables the user to monitor the at least one stimulation provided to the brain of the user by the brain interfacing apparatus, wherein the monitoring device is communicably coupled with the brain interfacing apparatus.

15 Claims, 3 Drawing Sheets

(51) Int. Cl.
  *A61B 5/291*  (2021.01)
  *A61B 5/372*  (2021.01)
  *A61B 5/377*  (2021.01)
  *G16H 10/60*  (2018.01)
  *G16H 20/30*  (2018.01)
  *G16H 40/40*  (2018.01)
  *G16H 40/67*  (2018.01)
  *G16H 50/20*  (2018.01)
  *G16H 70/40*  (2018.01)
  *A61B 5/383*  (2021.01)
  *G16H 20/10*  (2018.01)

(52) U.S. Cl.
  CPC ............ *A61B 5/377* (2021.01); *A61B 5/6803* (2013.01); *A61B 5/7267* (2013.01); *G16H 10/60* (2018.01); *G16H 20/30* (2018.01); *G16H 40/40* (2018.01); *G16H 40/67* (2018.01); *G16H 50/20* (2018.01); *G16H 70/40* (2018.01); *A61B 5/383* (2021.01); *G16H 20/10* (2018.01)

(56) References Cited

U.S. PATENT DOCUMENTS

| | | |
|---|---|---|
| 2012/0283526 A1 | 11/2012 | Gommesen et al. |
| 2013/0030317 A1 | 1/2013 | Tanner et al. |
| 2013/0079659 A1 | 3/2013 | Akhadov et al. |
| 2015/0105837 A1 | 4/2015 | Aguilar Domingo |
| 2017/0273611 A1 | 9/2017 | Purdon et al. |
| 2019/0021657 A1 | 1/2019 | Mohammadrezazadeh et al. |
| 2020/0155061 A1 | 5/2020 | Pradeep |
| 2021/0375480 A1* | 12/2021 | Mahon .................. G16H 20/30 |

FOREIGN PATENT DOCUMENTS

| | | | |
|---|---|---|---|
| CN | 116671935 A * | 9/2023 | |
| GB | 2579827 A * | 7/2020 | ............... A61B 5/24 |
| KR | 20080016303 A | 2/2008 | |
| KR | 20190058538 A | 5/2019 | |
| WO | 2012094621 A2 | 7/2012 | |
| WO | 2018213622 A1 | 11/2018 | |

OTHER PUBLICATIONS

International search report and written opinion of the International Searching Authority mailed in PCT Application PCT/IB2019/060767 on Mar. 23, 2020, 11 pages.

Search Report under Section17(5) issued in GB Application GB2009267.2 on Feb. 17, 2021, 8 pages.

Final Office Action issued for U.S. Appl. No. 17/413,310, on Mar. 13, 2024 , 18 Pages.

Office Action issued for Chinese Patent Application CN201980091609.5, on Nov. 15, 2023 , 10 Pages.

* cited by examiner

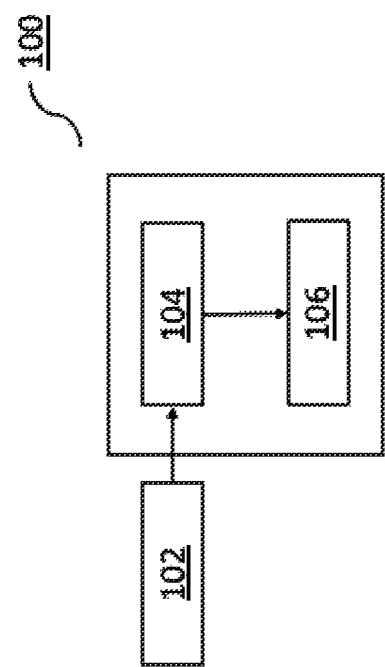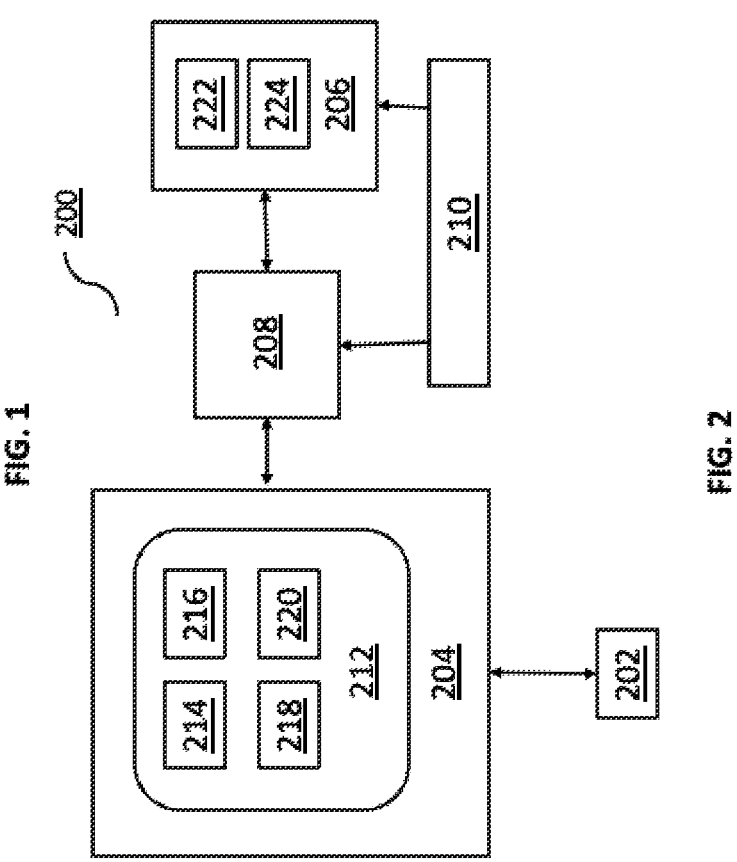

SYSTEM AND METHOD FOR IMPLEMENTING A STIMULATION PROTOCOL

CROSS-REFERENCE TO RELATED APPLICATIONS

This application is a continuation-in-part of U.S. patent application Ser. No. 17/413,310, titled "BRAIN INTERFACING APPARATUS AND METHOD" and filed on Jun. 11, 2021 which is incorporated herein by reference.

TECHNICAL FIELD

The present disclosure relates to systems for achieving desired therapeutic effect and methods of using such systems. More particularly, the present disclosure relates to a system for implementing a stimulation protocol that mimics an effect a drug has on the brain of a patient under treatment for a disease and methods for using such systems, for example by employing brain stimulation. Additionally, the present disclosure is concerned with computer programme products comprising a non-transitory computer-readable storage medium having computer-readable instructions stored thereon, the computer-readable instructions being executable by a computerised device comprising processing hardware to execute the aforesaid methods.

BACKGROUND

Currently, the treatment or stimulation protocols for any disease or condition are dominated by medications including various active pharmaceutical ingredients (APIs). The active pharmaceutical ingredients (APIs) are the chemical compound which are responsible for the therapeutic efficacy of the medicine. Generally, these APIs are systemic, one-fits-all and have associated side effects. Specifically, in most of the cases medication for a disease may have some adverse effect that leads to another disease or a problem. For example, treatment of diabetes using medication often has an adverse effect on the kidneys of the patients and causes problems related to the kidneys.

Another available treatment or stimulation protocol option includes use of electroceuticals. The "electroceuticals" are the controlled electrical impulses that target individual nerve fibres or specific brain circuits to treat an array of conditions.

One of the most commonly known electroceutical is the spinal cord stimulator by Boston Scientific used to treat pain. In a sense, it replaces the need to use opioids or indeed works where the opioids don't work. Another known electroceutical is the Deep Brain Stimulator used for Parkinson's disease, which works where the L-DOPA treatment is no longer effective and the symptoms are severe. However, the existing electroceutical devices block or stimulate with simple waveforms, rather than modulate dynamically on the millisecond scale.

Despite advancements that have been made in the aforementioned treatment protocols, electroceutical based treatment protocols need to be further optimised to achieve an improved real-time therapeutic effect. Therefore, in light of the foregoing discussion, there exists a need to overcome the aforementioned drawbacks associated with conventional electroceutical systems and treatment protocols.

SUMMARY

The present disclosure seeks to provide a system for implementing a stimulation protocol that mimics an effect of at least one drug on the brain of a user as treatment for a disease or condition.

Moreover, the present disclosure seeks to describe a method for using the system for implementing a stimulation protocol that mimics an effect of at least one drug on the brain of a user as treatment for a disease, physical and/or psychological condition.

An objective of the present disclosure is to provide a solution that overcomes at least partially the problems encountered in existing protocols and systems in prior art, and provides an improved system for implementing a stimulation protocol.

In a first aspect, embodiments of the present disclosure provide a system for implementing a stimulation protocol that, when in operation, mimics an effect of at least one drug on brain of a user under treatment for a disease, wherein the system comprises:
a brain interfacing apparatus that records electroencephalogram (EEG) of the user before and after taking the drug; wherein the brain interfacing apparatus comprises:
  a headwear arrangement to be placed or positioned on the head of the user wherein the headwear arrangement comprises an electrode arrangement including a plurality of electrodes that makes electrical contact with the scalp of the user, when in operation, to detect electrical signals therefrom and to apply brain stimuli thereto;
  an input/output arrangement that receives electrical signals from at least one of the plurality of electrodes and delivers the brain stimuli using brain stimulation protocol to the at least one of the plurality of electrodes, when in operation; and
  a data processing arrangement that processes the detected electrical signals received from the input/output arrangement, generates the brain stimulation protocol corresponding to the received electrical signals and provides at least one stimulation to the brain of the user, wherein the at least one stimulation is provided to achieve the effect similar to the at least one drug when in operation,
characterised in that the data processing arrangement compares the received electrical signals with electrical signals received after consumption of the drug to generate an analysis of the received electrical signals, wherein at least one adaptive learning algorithm is employed to generate the analysis of the received electrical signals, wherein the generated analysis of the received signal is used as a basis for generating the brain stimulation protocol corresponding to the received electrical signals Embodiments of the disclosure are advantageous in terms of providing a system for implementing a stimulation protocol, which has the potential of ensuring removal of side effects involved in medication based stimulation protocols, automating the treatment delivery, making the electroceuticals self-operable and easy to monitor. Furthermore, the system of the present disclosure provides a solution for achieving safe and effective stimulation protocol using stimulation(s), real-time monitoring of brain stimuli in accordance with the response received from the brain during the treatment.

In a second aspect, embodiments of the present disclosure provide a method of using a system for implementing a stimulation protocol that, when in operation, mimics an effect of at least one drug on brain of a user under treatment for a disease and/or for mental well-being applications, wherein the method comprises:

(i) using a brain interfacing apparatus to record electroencephalogram (EEG) of the user before and after taking the drug;

(ii) using a headwear arrangement to be placed or positioned on the head of the user to make electrical contact with the scalp of the user, and to detect electrical signals therefrom and to apply brain stimuli thereto;

(iii) using an input/output arrangement to receive electrical signals from at least one of the plurality of electrodes and deliver the brain stimuli using brain stimulation protocol to the at least one of the plurality of electrodes;

(iv) using a data processing arrangement to process the detected electrical signals received from the input/output arrangement, generate the brain stimulation protocol corresponding to the received electrical signals and provides at least one stimulation to the brain of the user, wherein the at least one stimulation is provided to achieve the effect similar to the at least one drug, wherein the data processing arrangement compares the received electrical signals with electrical signals received after consumption of the drug to generate an analysis of the received electrical signals, wherein at least one adaptive learning algorithm is employed to generate the analysis of the received electrical signals, wherein the generated analysis of the received signal is used as a basis for generating the brain stimulation protocol corresponding to the received electrical signals.

In another embodiment, the data processing arrangement compares the received electrical signals or the parameters derived from the received electrical signals with a predetermined reference data set to generate an analysis of the received electrical signals. Optionally, this may include a machine learning algorithm or other computational algorithms to update the processing used to generate a measure of a deviation of the detected electrical signal from an ideal reference signal or a set of parameters derived from the reference signal stored in the predetermined reference data set or of a reason for such deviation from the ideal reference signal.

In another aspect, embodiments of the present disclosure provide a system for implementing a stimulation protocol that, when in operation, mimics an effect of at least one or more compounds, such as a drug, a new chemical entity, a biological molecule, a natural stimulus substance, a nutraceutical, on brain of a user, wherein the system comprises:

a brain interfacing apparatus that records electroencephalogram (EEG) of the user before and after a given time interval wherein the brain interfacing apparatus comprises:

a headwear arrangement to be placed or positioned on the head of the user, wherein the headwear arrangement comprises an electrode arrangement including a plurality of electrodes that makes electrical contact with the scalp of the user, when in operation, to detect electrical signals therefrom and to apply brain stimuli thereto;

an input/output arrangement that receives electrical signals from at least one of the plurality of electrodes and delivers the brain stimuli using brain stimulation protocol to the at least one of the plurality of electrodes, when in operation; and a data processing arrangement that processes the detected electrical signals received from the input/output arrangement, generates the brain stimulation protocol corresponding to the received electrical signals and provides at least one stimulation to the brain of the user, wherein the at least one stimulation is provided to achieve the effect similar to the at least one drug when in operation, wherein the data processing arrangement compares the received electrical signals with electrical signals received after consumption of the drug to generate an analysis of the received electrical signals, wherein at least one adaptive learning algorithm is employed to generate the analysis of the received electrical signals, wherein the generated analysis of the received signal is used as a basis for generating the brain stimulation protocol corresponding to the received electrical signals.

In a forth aspect, embodiments of the present disclosure provide a computer programme product comprising a non-transitory computer-readable storage medium having computer-readable instructions stored thereon, the computer-readable instructions being executable by a computerised device comprising processing hardware to execute the aforementioned method.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary embodiments of the disclosure are shown in the drawings. However, the present disclosure is not limited to specific methods and instrumentalities disclosed herein. Moreover, those skilled in the art will understand that the drawings are not to scale. Wherever possible, like elements have been indicated by identical numbers.

Embodiments of the present disclosure will now be described, by way of example only, with reference to the following diagrams wherein:

FIG. 1 is a schematic illustration of a block diagram of a system for implementing a stimulation protocol that mimics an effect of at least one drug on the brain of a user under treatment for a disease, in accordance with an embodiment of the present disclosure;

FIG. 2 is a schematic illustration of a block diagram of a brain interfacing apparatus, in accordance with an embodiment of the present disclosure;

Figure 3A:
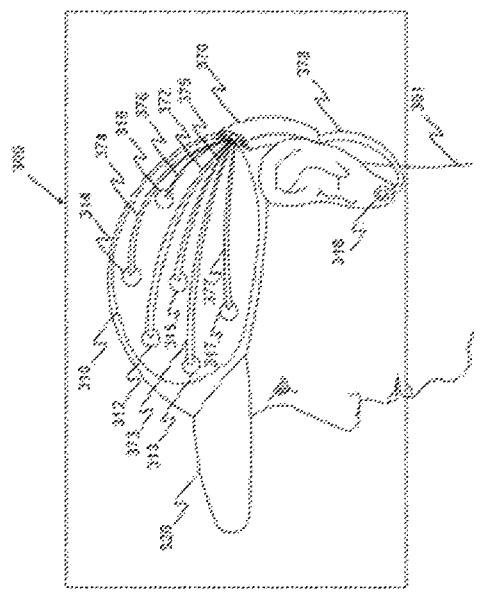
FIGS. 3A and 3B are illustrations of exemplary implementations of the brain interfacing apparatus of FIG. 1 applied on a user, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item to which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognise that other embodiments for carrying out or practising the present disclosure are also possible.

In a first aspect, embodiments of the present disclosure provide a system for implementing a stimulation protocol that, when in operation, mimics an effect of at least one drug on a brain of a user under treatment for a disease or for mental well-being applications, wherein the system comprises:

a brain interfacing apparatus that records electroencephalogram (EEG) of the user before and after taking the drug; and
  a headwear arrangement to be placed or positioned on the head of the user wherein the headwear arrangement comprises an electrode arrangement including a plurality of electrodes that makes electrical contact with the scalp of the user, when in operation, to detect electrical signals therefrom and to apply brain stimuli thereto;
  an input/output arrangement that receives electrical signals from at least one of the plurality of electrodes and delivers the brain stimuli using brain stimulation protocol to the at least one of the plurality of electrodes, when in operation; and
  a data processing arrangement that processes the detected electrical signals received from the input/output arrangement, generates the brain stimulation protocol corresponding to the received electrical signals and provides at least one stimulation to the brain of the user, wherein the at least one stimulation is provided to achieve the effect similar to the at least one drug when in operation,
wherein the data processing arrangement compares the received electrical signals with electrical signals received after consumption of the drug to generate an analysis of the received electrical signals, wherein at least one adaptive learning algorithm is employed to generate the analysis of the received electrical signals, wherein the generated analysis of the received signal is used as a basis for generating the brain stimulation protocol corresponding to the received electrical signals.

In another aspect, embodiments of the present disclosure provide a method of using a system for implementing a stimulation protocol that, when in operation, mimics an effect of at least one drug on a brain of a user under treatment for a disease, wherein the method comprises:
  (i) using a brain interfacing apparatus to record electroencephalogram (EEG) of the user before and after taking the drug;
  (ii) using a headwear arrangement to be placed or positioned on the head of the user to make electrical contact with the scalp of the user, and to detect electrical signals therefrom and to apply brain stimuli thereto;
  (iii) using an input/output arrangement to receive electrical signals from at least one of the plurality of electrodes and deliver the brain stimuli using brain stimulation protocol to the at least one of the plurality of electrodes;
  (iv) using a data processing arrangement to process the detected electrical signals received from the input/output arrangement, generate the brain stimulation protocol corresponding to the received electrical signals and provides at least one stimulation to the brain of the user, wherein the at least one stimulation is provided to achieve the effect similar to the at least one drug,
wherein the data processing arrangement compares the received electrical signals with electrical signals received after consumption of the drug to generate an analysis of the received electrical signals, wherein at least one adaptive learning algorithm is employed to generate the analysis of the received electrical signals, wherein the generated analysis of the received signal is used as a basis for generating the brain stimulation protocol corresponding to the received electrical signals.

The present disclosure provides the aforementioned apparatus and the aforementioned method for implementing a stimulation protocol that, when in operation, mimics an effect of at least one drug on the brain of a user as treatment for a disease or condition. The system disclosed herein is simple, robust, inexpensive, and allows real time monitoring of brain activity during treatment. The system efficiently ensures mimicking of the effect of the drug, in a manner that is robust, effective, and adaptive.

In an embodiment, the system further comprises measuring differences between the EEG before and after taking the drug and analyses them using at least one of adaptive learning algorithms.

In an embodiment, the analysis of the differences between the EEG before and after taking the drug are sent or retrieved from a database of EEG signals.

In an embodiment, the stimulation protocol is determined using at least one of adaptive learning algorithms in real time. Throughout the present disclosure, the term "user" as used herein relates to any person (i.e., human being) using the aforesaid system. Optionally, the user may be a person suffering from some specific medical or non medical conditions. More optionally, the user may be a person having a certain physical or mental disorder such as epilepsy, a head injury, encephalitis, brain tumour, encephalopathy, memory related problems, sleep disorders, stroke, dementia, etc.

Throughout the present disclosure, the term "treatment protocol" as used herein relates to a medication or electroceutical based treatment procedure or methodology used for stimulating the user suffering from specific disease or for improving mental wellness and mental or physical abilities of otherwise healthy individuals.

Throughout the present disclosure, the term "brain activity monitoring" as used herein relates to monitoring of electrical signals received from the brain by a method of electroencephalography (EEG). Optionally, the brain activity monitoring may include detection of signals which include, but are not limited to, signals, or a combination of signals, obtained using electric field encephalography (EFEG), Near infrared spectroscopy (NIRS), Magnetoencephalography (MEG), Electromyography (EMG) including signals coming from electrodes located spatially remote from the given user's scalp, Electrocardiography (ECG), eye tracking and/or Functional magnetic resonance imaging (fMRI). More optionally, the brain activity monitoring relates to monitoring of a change in electrical activity of the brain of a user, upon providing external electrical stimulus to the brain of the user. More optionally, the electrical activity of the brain of a user may be indicative of biological parameters related to the mental and physical health of a user including, but not limited to, a heart rate, a breathing rate and a skin conductance.

The brain interfacing apparatus pursuant to the present disclosure comprises a headwear arrangement including the plurality of electrodes. In use, the plurality of electrodes is placed or positioned on the scalp of the user, in order to provide the means for generating weak electric fields inside the brain of the user. Such electrical contact establishes an electrical path to detect electrical signals generated by the neurons and to provide brain stimuli to the neurons and/or other cells present inside the brain of the user. The plurality of electrodes detects the electrical signals generated inside the brain of the user by activity of neurons, wherein the detected electrical signals are provided to the input/output arrangement. Generally, the amplitude of the detected electrical signals ranges between 1 microvolt to 100 microvolts. More preferably, the range of the amplitude of the electrical signal is 2 microvolts to 65 microvolts. More preferably, the range is 4 microvolts to 50 microvolts. Most preferably, the range is 5 microvolts to 20 microvolts. The plurality of electrodes may optionally be configured as any suitable EEG electrode arrangement known in the art.

In pursuant to the present disclosure the monitoring device, when in operation is communicably coupled with the brain interfacing apparatus and enables a person using the system to monitor at least one parameter associated with the brain stimulation provided to the user.

In an embodiment, the monitoring device may be a display device, the input device includes at least one of a smartphone, a computer (can be personal, cloud-based, distributed or a tablet computer), a smart-watch, a remote control, a medical device, a local server, a server arrangement (such as, an arrangement of two or more servers communicably coupled with each other), a cloud server and a quantum computer.

Beneficially, the input devices provide a better interaction with the subject through a user-friendly interface. Additionally, the input devices enable the subject to answer the questions asked by a person using the intervention system, in real time manner.

Throughout the present disclosure, the terms "headwear" or "headwear arrangement" as used herein relate to an element of clothing which is worn by the user on his/her head. Optionally, the headwear arrangement may include, but not be limited to, any one of a cap, a hat, a helmet, headphones, a headband, glasses or a bonnet. More optionally, the headwear arrangement may be fabricated in a manner such that it comprises a layer of electrically insulating material. In an example, the headwear arrangement can be fabricated from one of materials including, but not limited to, wool, cotton, polyester, rubber, lycra, nylon or buckram. More optionally the term may also include elements of clothing worn on other parts of the body or even outside the body, but serving the same purpose of monitoring physiological parameters (or modulating these parameters where applicable), such as watch, wrist straps, chest straps, as well as temperature sensors and external laser, magnetic and electromagnetic detectors of physiological parameters.

Throughout the present disclosure, the term "brain stimulus" or "brain stimuli" (plural of "stimulus") as used herein relates to an external electrical current or to a defined sequence or multiple sequences of electric current amplitudes between a pair, several pairs or any combination of the electrodes applied to the scalp of a user or to locations spatially remote from the scalp of a user, in order to modify and/or enhance an electrical activity in the brain of the user or in the nervous tissues that the current is able to reach. Moreover, in an example, brain stimuli applied to the scalp of the user are analogue external electrical signals having a voltage in a range of 1 millivolt to 50 volts and having a current in a range of 0.1 milliampere to 20 milliamperes. The range of voltage is 40V to 50V, wherein the voltage is function of interface connection which describes the quality of connection of plurality of electrodes with scalp. Furthermore, the range of current is 1 milliampere to 10 milliamperes in respect of short waveforms. Additionally, the range of current is 0.3 milliampere to 1 milliampere depending upon the type of waveforms. More preferably, the range of current is 0.6 milliampere to 1 milliamperes. Alternatively, the term could refer to magnetic fields or ultrasonic waves applied to the brain of the user as a sequence or multiple sequences of signals capable of modifying brain activity.

Throughout the present disclosure, the term "stimulation" as used herein relates to altering (referring to raising, lowering or otherwise modulating) levels of physiological or nervous activity in the brain or in the tissues spatially remote from the given user's brain. Notably, the stimulation of the brain of the user is carried out with help of electrical, magnetic or ultrasonic signals, applied to the scalp of the user with the help of one or more electrodes, magnetic coils or ultrasound wave generators. Further, stimulation of the brain is achieved by using any one of minimally invasive brain stimulation or non-invasive brain stimulation methods, or optionally both. More broadly the term may include activities modulating the brain activity that do not require electric or electromagnetic interference, such as light stimulation, binaural beats or even breathing and meditation exercises.

Throughout the present disclosure, the term "electrodes" as used herein relates to one or more electrical conductors, with the materials of these conductors including, but not limited to stainless steel, platinum, silver chloride-coated silver, carbon rubber, graphene and other metamaterials, as well as hydrogels, silicone, sponges, foam or any absorbent with a conducting medium, where necessary to be placed between the conductors and the scalp or skin, including, but not limited to electrically conductive gels and pastes (such as Ten20 paste), as well as liquids (such as physiological saline solution) with such an ionic composition as to establish an electrical path to detect electrical signals generated by the neurons inside the brain and to provide brain stimuli to the neurons and/or other cells present inside the brain of the user. Furthermore, the electrodes are operable to convert an ionic potential into an electric potential and to induce electromagnetic fields on the scalp and inside the skull. Moreover, the electrodes can be of minimally invasive (such as needle electrodes or micro electrodes) or non-invasive type (such as surface electrodes), or optionally both. In an example, the electrodes comprise an assembly of saline-soaked foam, conductive carbon and a metal contact. In such an example, the metal contact is operatively coupled with one or more components of the brain interfacing apparatus (such as, an input/output arrangement and/or a data processing arrangement, described in detail herein later). Alternatively, the term could refer to magnetic coils or ultrasonic wave generators necessary for modifying the brain activity during transcranial magnetic or ultrasonic stimulation.

Throughout the present disclosure, the term "input/output arrangement" as used herein relates to programmable and/or non-programmable components that, when in operation, receive, modify, convert, process or generate one or more types of signals. Optionally, the input/output arrangement is implemented as a hardware or a software, or a combination thereof.

Throughout the present disclosure, the term "data processing arrangement" as used herein relates to programmable and/or non-programmable components that, when in operation, execute one or more software applications for storing, processing and/or sharing of data and/or a set of instructions. Optionally, the data processing unit can include, for example, a component included within an electronic communications network. Furthermore, the data processing arrangement may include hardware, software, firmware or a combination of these, suitable for storing and processing various information and services accessed by the one or more user using the one or more user equipment. Optionally, the data processing arrangement may include functional components, for example, a processor, a memory, a network adapter and so forth. For example, the data processing arrangement can be implemented using a computer, a phone (for example, a smartphone), a local server, a server arrangement (such as, an arrangement of two or more servers communicably coupled with each other), a cloud server, a quantum computer and so forth. Throughout the present disclosure, the term "memory module" as used herein relates to a volatile or persistent medium, such as an electrical circuit, magnetic disk, virtual memory or optical disk, in which a computer and/or a data processing arrangement may store data for any duration. Optionally, the memory module may be a non-volatile mass storage such as physical storage media.

Throughout the present disclosure, the term "power unit" as used herein relates to a power source being configured to provide electrical power to one or more components of the brain interfacing apparatus. Optionally, the power unit may include one or more cells or batteries capable of providing electrical power. In an example, the power unit may provide 12 Volts electrical supply to a stimuli generator in the input/output arrangement and 5 Volts electrical supply to the data processing arrangement. Optionally, the power unit may also include a power boost generator and regulator circuitry to turn a 3.7 V supply from a battery into a 5 V supply for the brain interfacing apparatus and a 12-40 V supply for the stimuli generator. Optionally, the power unit may also contain circuitry that includes a voltage splitter to provide +/−12-40 V to the stimuli generator.

Throughout the present disclosure the term "real-time" refers to any process or a set of processes that are being executed concurrently or in a temporally alternating manner with a small time lag in between these alternations. Moreover, where a set of processes must be executed in a sequential manner, the term "concurrently" would refer to the processes being executed in parallel with a minimal delay/time-shift relative to each other.

Throughout the present disclosure, the term "brain stimulation protocol" as used herein, refers to an electrical signal containing information about brain stimuli to be generated. It should be noted that in an embodiment of the present invention where the plurality of electrodes includes electrodes placed at locations remote from the given user's scalp, the brain stimulation protocol may also include information about the stimuli to be generated at these electrodes. It should also be noted that the brain stimulation protocol also refers to the information that may change throughout the duration of the stimulation as a result of the process of optimisation described in the present disclosure. For example, the information includes one or more electrical characteristics for each electrode, such as an amplitude, a time-period, a phase, one or more frequencies and the power of these frequencies giving rise to a specific sequence of brain stimuli to be generated. The generated brain stimuli will be in the form of a defined sequence or multiple sequences of electric current amplitudes between a pair, several pairs or any combination of the electrodes. Optionally, the brain stimulation protocol includes the time duration for which brain stimuli have to be applied to the scalp of the user. Optionally, the brain stimulation protocol refers to information about at least one of: a visual stimulation, an audio stimulation, a virtual reality stimulation and/or a set of breathing or meditation instructions to be generated and provided to the user.

Optionally, the plurality of electrodes may include separate electrodes configured for EEG recording and electrical stimulation respectively. Alternatively, the electrode arrangement may include a separate electrode for each location at which it may be desirable to detect EEG signals and/or provide electrical stimulation.

In an embodiment, the plurality of electrodes is in electrical contact with an appreciable area of a given user's scalp; for example, the electrodes may be user-replaceable electrodes and may be lightly spring-loaded to provide a positive contact onto the user's scalp when the headwear arrangement is worn by the user. More optionally, the end of the electrodes may include a 2-D array of small pointed sub-electrodes modified with conducting medium to safely deliver sufficient current, wherein the end could have an area of any size including, but not limited to 4 mm×4 mm, but other appropriate areas could be used, and the sub-electrodes are pointed and can find a path between hairs of the scalp to make contact onto skin of the scalp. Specifically, the plurality of electrodes is spatially located such that the voltage applied across the electrodes generates the electromagnetic field in specific parts of the brain.

Furthermore, the plurality of electrodes, when actively delivering current and when in contact with the scalp of the user, apply electromagnetic fields to the brain of the user acting as brain stimuli. Such brain stimuli are provided with the help of generated brain stimulation protocols received by the input/output arrangement from the data processing arrangement. The generated brain stimulation protocols received from the data processing arrangement are processed by the input/output arrangement, namely converted, into an analogue form and adjusted to a desired current amplitude, before being applied as brain stimuli to the scalp of the user.

The data processing arrangement uses at least one adaptive learning algorithm or other computational algorithms implemented as at least one of the executable software and the digital hardware (e.g. FPGA, ASIC, custom hardware Silicon chip design). Furthermore, the at least one adaptive learning algorithm may include at least one of a hardware, executable software or a digital hardware (e.g. FPGA, ASIC, custom Silicon chip design) configured to use the technology of real-time adaptation of brain stimuli in a manner that minimises the latency between signal processing and generation of the brain stimulation protocol. Moreover, the data processing arrangement, including adaptive learning algorithms, keeps track of the effects that the various brain stimulation protocols have on the brain of the user. Furthermore, such data processing arrangement is versatile enough to analyse its own actions and consequently utilise at least one of the adaptive learning algorithms or other computational algorithms to optimise the brain stimulation protocol based on the more relevant training datasets. Moreover, the training datasets may include, but are not limited to, previous action records, data from plurality of other similar systems, predetermined reference data and historical data. In an embodiment, the brain interfacing apparatus implementing the adaptive learning algorithm is configured to record and extract one or more potential target marker for neuromodulation. Optionally, the one or more potential target markers are the changes or activities caused in the brain of the user in the forms of a change of brainwaves or reduction of response to painful stimuli, wherein the changes or activities are caused in response to use of one or more drug injected to the user. In an embodiment, the one or more potential target markers are stored in databases for implementation of artificial intelligence algorithms. The brain interfacing apparatus is capable of delivering and optimising a brain stimulation protocol to induce effects similar to those induced by drugs affecting specific neuronal receptors. Beneficially, such optimal stimulation helps in inhibiting or potentiating activities similar to drugs without their side effects. In another embodiment, the brain interfacing apparatus implementing the adaptive learning algorithm is configured to stimulate or mimic the changes or activities caused in the brain of the user in the forms of a change of brainwaves based on the recorded target markers. Therefore, the use of the device and the algorithms (i) for recording and extracting potential target markers for neuromodulation; (ii) for modulating brain waves, event-related potentials or other signals to mimic the changes achieved by drugs; (iii) to enhance the effects of drugs; (iv) to reduce the unwanted side effects of drugs on the brain activity has implications for replacement of regular drugs such as opiates, or other benefits in medical conditions.

In an embodiment the plurality of electrodes used for providing the brain stimuli to the brain of the user, may be arranged in one pair, in more than one pair or in any combination of stimulating electrodes as determined by the brain stimulation protocol.

The input/output arrangement includes an input signal processing arrangement comprising a pre-processor and an input converter. The input signal processing arrangement, when in operation, processes and/or modifies electrical signals received from the brain of the user. Optionally, the pre-processor includes an amplifier, more specifically it may include a programmable gain amplifier, which stabilises the electrical signals received from the brain and amplifies the signals by an amplification factor in a range of 2× to 100× for obtaining an amplified signal, wherein 2× amplification factor is used for a very high dynamic range of analogue to digital conversion for the option of digital pre-processing and artefact subtraction. Optionally, the pre-processor may include one or more analogue filters (such as an electrical noise filter or the stimulation artefact filter) to reduce specific artefacts and/or noise. The electrical signals received form the brain are time-varying, namely are analogue in nature. However, the data processing arrangement only understands (namely, processes) digital bits, therefore it is essential to convert the received electrical signal (analogue in nature) from the brain to digital bits, so that the data processing arrangement is able to understand (namely, process) the received electrical signals from the brain after analogue to digital conversion. The input converter receives the amplified signal and converts it into a form suitable for analysing and processing. Thus, the input converter includes an analogue-to-digital converter. In an example, the input signal processing arrangement receives analogue electrical signals having an amplitude in a range of 1 microvolt to 12 Volts from the scalp of the user and the pre-processor eliminates some artefacts and noise and amplifies the signals to generate corresponding amplified signals having amplitudes in a range of up to 12 V. Subsequently, the amplified signals are converted into corresponding digital signals having a sequence of discrete values representative of the corresponding range.

The input/output arrangement further includes an output converter and a stimuli generator. In operation, a brain stimulation protocol is received from the data processing arrangement which is communicably coupled with the input/output arrangement. The received brain stimulation protocol is in the form of digital or discrete signal. Furthermore, the received brain stimulation protocol is sent to the output converter wherein, the output converter converts the received brain stimulation protocol into an analogue signal having varying voltage amplitude with respect to time. The stimuli generator receives the converted analogue signals from the output converter and may optionally convert the set voltage signals into defined current signals. The output of the stimuli generator is acting as brain stimuli and the generated brain stimuli are applied to the scalp of the user through one pair, more than one pair or any combination of stimulating electrodes as determined by the brain stimulation protocol. Optionally, the stimuli generator is an isolated stimuli generator powered by a separate power unit, a constant current stimulator or V-to-I converter. Alternatively, the input/output arrangement may be connected with a constant voltage source. Where the brain stimulation is performed by modalities other than electrical, the input/output arrangement is modified accordingly.

The data processing arrangement includes a processing unit and a memory module. The memory module comprises a predetermined reference data set or a set of parameters derived therefrom. Optionally, the predetermined reference data set may include EEG recordings of or data derived from EEG recordings from a plurality of persons, wherein the EEG recording is present in the form of digital electrical signals, or data that is representative thereof.

The data processing arrangement processes the detected electrical signals received from the input/output arrangement and generates the brain stimulation protocol corresponding to the received electrical signals, when in operation. Optionally, the data processing unit employs adaptive learning algorithms for processing and analysing the detected electrical signals received from the input/output arrangement. Optionally, the processed electrical signals received from the input/output arrangement are compared with one or more EEG recordings of a predetermined reference data set present in the memory module.

The brain interfacing apparatus further comprises one or more power units. The power units are electrically coupled with the input/output arrangement and the data processing arrangement and supply electrical power to the input/output arrangement and the data processing arrangement, when in operation. Optionally, the power unit may include at least one of the following sources including, but not limited to: a nickel-cadmium (NiCd), a nickel-zinc (NiZn), a nickel metal hydride (NiMH), a solid-state battery (for example, a ceramic-based battery, a glass-based battery or a sulphide-based battery) and a lithium-ion (Li-ion) or lithium-polymer (Lipo) battery, as well as a generator of power from sources like movement or solar energy, a receiver for one of wireless power transfer technologies, or a surge protected input from the mains.

In an embodiment, the brain interfacing apparatus comprises at least two power units for providing an isolated electrical power to an input portion (comprising units/arrangements responsible for recording or monitoring and processing of electrical signal received form the brain of the user) and an output portion (comprising units/arrangements responsible for the generation of the brain stimuli) the input/output arrangement, respectively.

In an embodiment, the one or more power units are operable to supply electrical power to the brain interfacing apparatus on receiving an instruction from the user via the control unit. Moreover, the user may provide the brain interfacing apparatus with an instruction to switch "ON" the electrical power supply to the brain interfacing apparatus, after wearing the headwear arrangement for initialising the operation of the brain interfacing apparatus. Optionally, the one or more power units are operable to automatically switch "ON" the electrical power supply to the brain interfacing apparatus, in a situation when the user wears the headwear arrangement of the brain interfacing apparatus.

In an embodiment, the data processing arrangement may analyse the received electrical signals in a real-time manner, so that the electrical signals are detected at the user's scalp concurrently with the brain stimuli being applied to the brain of the user.

In an example, electrical signals received from the input signal processing arrangement, before consumption of the drug by the user, are stored in a memory module. Further, after a compound such as a drug, new chemical entity, biological molecule, nutraceutical, naturally occurring substance, is consumed by the user has started to exert its effects, the electrical signals received from the input signal processing arrangement are sent to the data processing arrangement for comparison with the electrical signals received before consumption of the drug to generate an analysis of the received electrical signals, wherein at least one adaptive learning algorithm is employed to generate the analysis of the received electrical signals. This analysed information is used as a basis for subsequent stimulation. Once the effect of the e.g. drug has worn off and the user desires to reproduce the effect of the drug, at least one adaptive learning algorithm is employed to generate the brain stimulation protocol, based on the generated analysis, that mimics the effect of the drug. Thereafter, the brain stimulation protocol is transmitted to the signal generator of the input/output arrangement where the signal generator generates the brain stimuli corresponding to the received brain stimulation protocol from the data processing arrangement. Subsequently, the generated brain stimuli are applied to the scalp of the user by using the at least one electrode of the plurality of electrodes. Specifically, detection, processing and analysis of electrical signals received from the brain and application of the brain stimuli to the scalp of the user are carried out concurrently or simultaneously in such a manner that there is minimal lag in the aforesaid operation.

In an embodiment, the system includes a safety arrangement, wherein the safety arrangement disables the delivery of the brain stimuli to the electrode arrangement, in an event of an electrical malfunction of the apparatus or a request from the user to cease brain stimulation. Furthermore, the safety arrangement includes at least one of a protective relay, an over-current sensor, an over-voltage sensor, a frequency sensor, a sensor of excessive muscle/movement activity ("discomfort" sensor) and an emergency "kill" switch. Furthermore, the safety arrangement is communicably coupled to the control unit via the data processing arrangement, which in turn is also coupled to the third-party device with a user-friendly interface for aborting the stimulation/recording. Moreover, the safety arrangement, when in operation, receives data related to at least one of the current and voltage at the plurality of electrodes, from at least one of the over-current sensor and over-voltage sensor. Furthermore, in one of the implementations of the safety arrangement, when in operation, it determines an event of the electrical malfunction by comparing the data related to at least one of the current and voltage at the plurality of electrodes with a pre-determined reference data including a reference data related to at least one of the current and voltage at the plurality of electrodes.

Throughout the present disclosure, the term "electrical malfunction" as used herein relates to the undesirable amount of electrical current and/or electrical voltage occurring in the brain interfacing apparatus, wherein such undesirable amount of electrical current and/or electrical voltage may harm the user and/or the apparatus. Furthermore, in an event of the electrical malfunction, the safety arrangement is configured to cut-off the electrical power supply to the apparatus from the one or more power unit via the protective relay.

Beneficially, the safety arrangement provides enhanced protection from any damage to the user in real-time manner, resulting in risk-free usage of the brain interacting apparatus without any expert assistance. Moreover, the brain interfacing apparatus is designed in its external and internal component parts, and also in its manner of operation, in such a way that any occurrence of harm for the user is avoided.

The terms "mental wellness" or "mental well-being" refer to the scope of applications of the patent that do not fall under the medical treatment category. These include but are not limited to fatigue, stress, lack of focus, non-clinical depression, forgetfulness, irritability.

The present disclosure relates to a system comprising the brain interfacing apparatus which the user can wear overnight. The invention could potentially mimic a sleeping pill, via slow wave stimulation, or other waveforms determined by the algorithm. The system can, for example, be worn while sleeping over the course of 1-6 hours, with the voltage set to 5 V and with the current low. The invention could also potentially mimic a painkiller utilising a higher current in the range of 1-10 mA, over the course of a few minutes with the voltage changing according to the impedance.

The present disclosure also relates to the method as described above. Various embodiments and variants disclosed above apply mutatis mutandis to the method.

Optionally, the method includes using the brain interfacing apparatus to record the EEG and provide the at least one stimulation in a real time manner, so that the electrical signals are detected at the user's scalp concurrently with the brain stimuli being applied to the user.

Optionally, the method includes providing the at least one stimulation by implementing a predefined brain stimulation protocol. More optionally, the method includes providing the at least one stimulation periodically, based on a prescription provided by a medical practitioner.

Optionally, the method includes using a safety arrangement to disable the brain interfacing apparatus, in an event of a malfunction of the system.

In an embodiment, the present disclosure provides a computer programme product comprising a non-transitory computer-readable storage medium having computer-readable instructions stored thereon, the computer-readable instructions being executable by a computerised device comprising processing hardware to execute a method of using a brain interfacing apparatus that provides, when in operation, brain activity monitoring and stimulation of the brain of the user.

The present disclosure relates to method which is directed at the operation of the system for implementing the stimulation protocol. The method does not refer to steps involving the practice of applying a therapeutic treatment to a patient.

The present disclosure relates to the system for implementing stimulation protocol, wherein a function of a nervous system is modified by applying electrical stimulation to the nervous system to perform a task, or a different brain stimulation protocol is used to enhance performance of the nervous system for performing a cognitive task.

DETAILED DESCRIPTION OF THE DRAWINGS

Referring FIG. 1, there is shown a system 100 for implementing a stimulation protocol that, when in operation, mimics an effect of at least one drug on brain of a user 102 under treatment for a disease, in accordance with an embodiment of the present disclosure. As shown, the intervention system 100 comprises a brain interfacing apparatus 104 that records electroencephalogram (EEG) of the user 102 before and after taking the drug and provides at least one stimulation to the brain of the user 102, wherein the at least one stimulation is provided to achieve the effect similar to the at least one drug, and a monitoring device 106 that enables the user 102 to monitor the at least one stimulation provided to the brain of the user 102 by the brain interfacing apparatus 104, wherein the monitoring device 106 is communicably coupled with the brain interfacing apparatus 104.

Referring FIG. 2, there is a brain interfacing apparatus 200 (such as the brain interfacing apparatus 104 of FIG. 1) for providing brain stimulations to a plurality of subjects 202 (such as the user 102 of FIG. 1), in accordance with an embodiment of the present disclosure. As shown, the stimulation arrangement 200 comprises a headwear arrangement 204, a data processing arrangement 206, an input/output arrangement 208 and one or more power units 210. Furthermore, the headwear arrangement 204 comprises an electrode arrangement 212 including a plurality of electrodes 214 to 220, wherein the plurality of electrodes is arranged in a manner to make contact with the scalp of the user, for detecting the brain activity. Moreover, the electrode arrangement 212 is communicably coupled to the input/output arrangement 208, wherein the input/output arrangement 208, when in operation, receives the detected signals and delivers the brain stimuli to the at least one of the plurality of electrodes 214 to 220. Furthermore, the input/output arrangement 208 contains an optional input signal pre-processing arrangement (not shown), which can include an optional amplifier (not shown); an artefact filter (not shown); an input converter (not shown); an output converter (not shown) and stimuli generator (not shown). Furthermore, the input/output arrangement 208 is communicably coupled with the data processing arrangement 206. Moreover, the data processing arrangement 206 comprises a memory module 222 and a processing unit 224. The one or more power unit 210, when in operation, provides electrical power to the input/output arrangement 208 and the data processing arrangement 206.

Referring FIG. 3A, there is shown an exemplary implementation of the brain interfacing apparatus 300 (such as the brain interfacing apparatus 100 of FIG. 1) positioned on the head of the user 301, in accordance with an embodiment of the present disclosure. Specifically, the exemplary implementation is a side-view of the user 301 wearing the brain interfacing apparatus 300. The brain interfacing apparatus 300 comprises a headwear arrangement 320 and an assembly unit 370, wherein the headwear arrangement 320 is implemented using a sports cap in this example. Moreover, the headwear arrangement 320 comprises an electrode arrangement 310, wherein the electrode arrangement 310 comprises plurality of electrodes 312 to 318. Furthermore, the plurality of electrodes 312 to 318 are connected to the assembly unit 370 through a plurality of connecting wires 372 to 378, respectively. Specifically, one of the electrodes 318 of the plurality of the electrodes 312 to 318 is a reference electrode connected to a non-scalp portion of the head of the user 301.

Figure 3B:
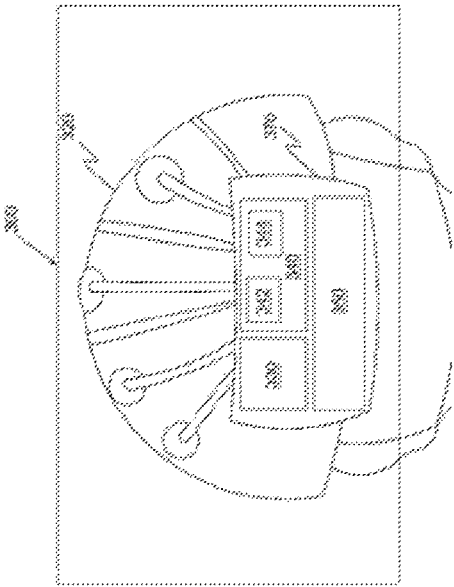

Referring FIG. 3B, there is shown the same exemplary implementation of the brain interfacing apparatus 300 placed on the head of the user 301, in accordance with an embodiment of the present disclosure. Specifically, the exemplary implementation is a back-view of the user 301 wearing the brain interfacing apparatus 300 comprising the headwear arrangement 320 and an assembly unit 370. Further, the assembly unit 370 comprises an input/output arrangement 330, a data processing arrangement 340 and one or more power unit 350. Moreover, the data processing arrangement 340 comprises a memory module 342 and a processing unit 344.

Figure 4:
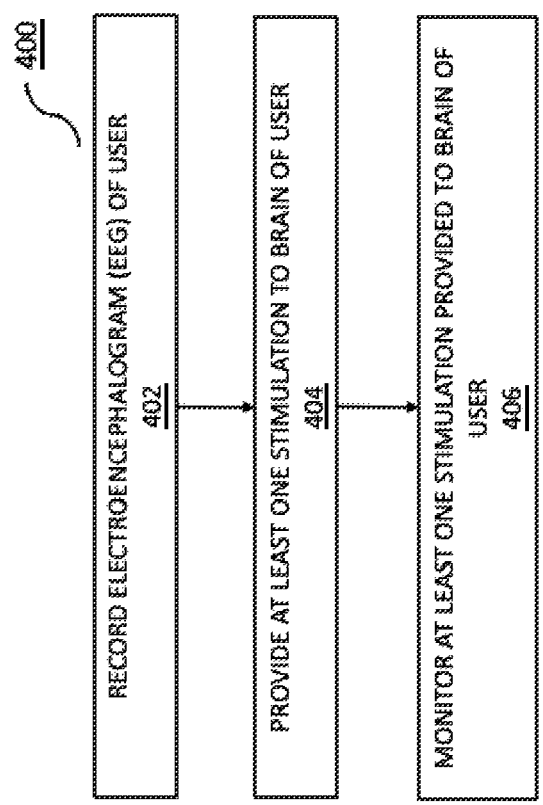
FIG. 4 is an illustration of steps of a method for (of) mimicking an effect of at least one drug on the brain of a user as treatment for a disease, in accordance with an embodiment of the present disclosure.

Referring to FIG. 4, illustrated are steps of a method 400 for mimicking an effect of at least one drug on the brain of a user (such as the user 102 of FIG. 1) under treatment for a disease, in accordance with an embodiment of the present disclosure. The method 400 initiates at a step 402, at the step 402, electroencephalogram of the user 102 is recorded using a brain interfacing apparatus (such as the brain interfacing apparatus 104 of FIG. 1), before and after taking the drug. At a step 404 at least one stimulation to the brain of the user 102 using the brain interfacing apparatus 104. At a step 406 stimulation provided to the brain of the user 102 is monitored using a monitoring device (such as the monitoring device 106 of FIG. 1). At the step 406 the method 400 ends.

The steps 402 to 406 of method 400, are only illustrative and other alternatives can also be provided where one or more steps are added, one or more steps are removed, or one or more steps are provided in a different sequence without departing from the scope of the claims herein.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural where appropriate.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

The invention claimed is:

1. A system for implementing a stimulation protocol that, when in operation, mimics an effect of at least one drug on a brain of a user, wherein the system comprises:
a brain interfacing apparatus that records electroencephalogram (EEG) of the user before and after taking the at least one drug, wherein the brain interfacing apparatus comprises:
a headwear arrangement to be placed or positioned on the head of the user wherein the headwear arrangement comprises an electrode arrangement including a plurality of electrodes that makes electrical contact with scalp of the user, when in operation, to detect electrical signals therefrom and to apply brain stimuli thereto;

an input/output arrangement that receives electrical signals from at least one of the plurality of electrodes and delivers the brain stimuli using the brain stimulation protocol to the at least one of the plurality of electrodes, when in operation; and a data processing arrangement that processes the detected electrical signals received from the input/output arrangement, generates the brain stimulation protocol corresponding to the received electrical signals and provides at least one stimulation to the brain of the user, wherein the at least one stimulation is provided to achieve the effect similar to the at least one drug when in operation, wherein the data processing arrangement compares the received electrical signals with electrical signals received after consumption of the at least one drug to generate an analysis of the received electrical signals, wherein at least one adaptive learning algorithm is employed to generate the analysis of the received electrical signals, wherein the generated analysis of the received signal is used as a basis for generating the brain stimulation corresponding to the received electrical signals, wherein the system further comprises measuring differences between the EEG before and after taking the at least one drug and analyses them using the at least one of adaptive learning algorithms, and wherein the brain interfacing apparatus, when in operation, provides the at least one stimulation by implementing a predefined brain stimulation protocol.

2. The system of claim 1, wherein the analysis of the differences between the EEG before and after taking the at least one drug is sent or retrieved from a database of EEG signals.

3. The system of claim 2, wherein the stimulation protocol is determined using the at least one of adaptive learning algorithms in real time.

4. The system of claim 2, wherein the brain interfacing apparatus, when in operation, records the EEG and provides the at least one stimulation in a real time manner, so that the electrical signals are detected at the scalp of the user concurrently with the brain stimuli being applied to the user.

5. The system of claim 1, wherein the at least one stimulation is provided periodically, based on prescription provided by a medical practitioner.

6. The system of claim 1, wherein the system includes a safety arrangement, wherein the safety arrangement disables brain interfacing apparatus, in an event of a malfunction of the system.

7. The system of claim 1, wherein the input/output arrangement is configured to include:
an input signal processing arrangement comprising a pre-processor and an input converter for at least one of processing and modifying the electrical signals received from the brain of the user; and
an output converter and a stimuli generator, wherein the output converter is configured to convert the received brain stimulation protocol into an analogue signal having a varying voltage amplitude with respect to time, for applying to the scalp of the user.

8. The system of claim 1, wherein the data processing arrangement is configured to include the at least one adaptive learning algorithm implemented as at least one of an executable software product and digital hardware, wherein the data processing arrangement is configured to analyse its own actions and to use the at least one adaptive learning algorithm to optimize the brain stimulation protocol based on one or more relevant training datasets.

9. A method of using a system for implementing a stimulation protocol that, when in operation, mimics an effect of at least one drug on a brain of a user, wherein the method comprises:
(i) using a brain interfacing apparatus to record electroencephalogram (EEG) of the user before and after taking the at least one drug;
(ii) using a headwear arrangement to be placed or positioned on the head of the user to make electrical contact with scalp of the user, and to detect electrical signals therefrom and apply brain stimuli thereto;
(iii) using an input/output arrangement to receive electrical signals from at least one of a plurality of electrodes and deliver the brain stimuli using brain stimulation protocol to the at least one of the plurality of electrodes;
(iv) using a data processing arrangement to process the detected electrical signals received from the input/output arrangement, to generate the brain stimulation protocol corresponding to the received electrical signals and to provide at least one stimulation to the brain of the user, wherein the at least one stimulation is provided to achieve the effect similar to that at least one drug, wherein the data processing arrangement compares the received electrical signals with electrical signals received after consumption of the at least one drug to generate an analysis of the received electrical signals, wherein at least one adaptive learning algorithm is employed to generate the analysis of the received electrical signals, wherein the generated analysis of the received signal is used as a basis for generating the brain stimulation protocol corresponding to the received electrical signals, wherein the method further comprises measuring differences between the EEG before and after taking the at least one drug and analyses them using the at least one of adaptive learning algorithms, and wherein the method further comprises providing the at least one stimulation by implementing a predefined brain stimulation protocol.

10. The method of claim 9, wherein the analysis of the differences between the EEG before and after taking the drug is sent or retrieved from a database of EEG signals.

11. The method of claim 9, wherein the stimulation protocol is determined using the at least one of adaptive learning algorithms in real time.

12. The method of claim 9, wherein the method includes using the brain interfacing apparatus to record the EEG and provide the at least one stimulation in a real time manner, so that the electrical signals are detected at the scalp of the user concurrently with the brain stimuli being applied to the user.

13. The method of claim 9, wherein the method includes providing the at least one stimulation periodically, based on a prescription provided by a medical practitioner.

14. The method of claim 9, wherein the method includes using a safety arrangement to disable the brain interfacing apparatus, in an event of a malfunction of the system.

15. A computer program product comprising a non-transitory computer-readable storage medium having computer-readable instructions stored thereon, the computer-readable instructions being executable by a computerized device comprising processing hardware to execute the method of claim 9.

\* \* \* \* \*